(12) United States Patent
Berreth

(10) Patent No.: US 8,208,702 B2
(45) Date of Patent: Jun. 26, 2012

(54) METHOD FOR PROVIDING IMAGE OBJECTS IN A MEDICAL IMAGE INFORMATION SYSTEM, AND MEDICAL IMAGE INFORMATION SYSTEM

(75) Inventor: Marc Berreth, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 921 days.

(21) Appl. No.: 12/232,448

(22) Filed: Sep. 17, 2008

(65) Prior Publication Data
US 2009/0074274 A1    Mar. 19, 2009

(30) Foreign Application Priority Data
Sep. 19, 2007    (DE) .................... 10 2007 044 599

(51) Int. Cl.
*G06K 9/00* (2006.01)
(52) U.S. Cl. ........................................... 382/128
(58) Field of Classification Search .......... 382/128–132, 382/232, 235, 305; 600/437
See application file for complete search history.

(56) References Cited

U.S. PATENT DOCUMENTS

| | | | |
|---|---|---|---|
| 6,381,029 B1 | 4/2002 | Tipirneni | |
| 6,621,918 B1 | 9/2003 | Hu | |
| 2005/0111711 A1* | 5/2005 | Deaven et al. | 382/128 |
| 2005/0254729 A1* | 11/2005 | Saito et al. | 382/305 |

OTHER PUBLICATIONS

"IVCA Technical Paper", Mar. 16, 1996, über (web.archive.org, Stand vom Oct. 24, 1997) URL: http://www.citrix.com/technology/icatech.htom, Germany Office Action Issued Jul. 8, 2008.

* cited by examiner

*Primary Examiner* — Irakli Kiknadze
(74) *Attorney, Agent, or Firm* — Harness, Dickey & Pierce, P.L.C.

(57) ABSTRACT

A medical image information system is disclosed which includes a PACS server having at least one non-volatile data storage device for storing the image objects, a terminal server which is connected to the PACS server for data purposes, and at least one terminal client which is connected to the terminal server for data purposes. In at least one embodiment, a text data application, which is used solely to manage text data of image objects, is implemented in the terminal client, and an image data application, which is used solely to manage pixel-based image data of image objects, is implemented in the terminal server. A method is also disclosed for providing image objects in the image information system. In at least one embodiment, an image object which is stored in the PACS server is transmitted to the terminal server, in particular on the basis of a user request, under the control of the image data application, pixel-based screen contents for a graphical display of the image object by the terminal client, under the control of the image data application, are determined by the terminal server, and the screen contents for the image object, which are determined by the terminal server, are displayed by the terminal client.

10 Claims, 1 Drawing Sheet

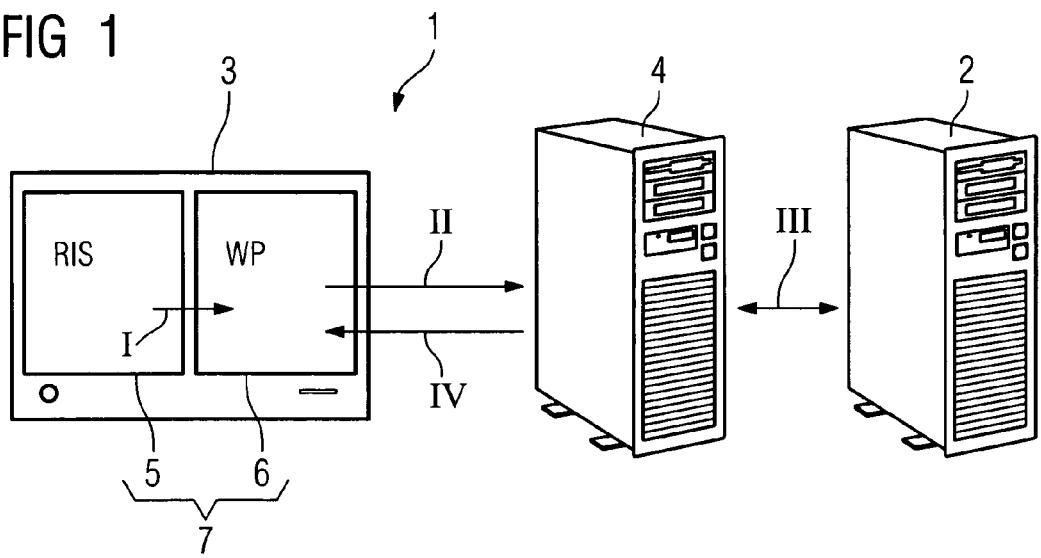
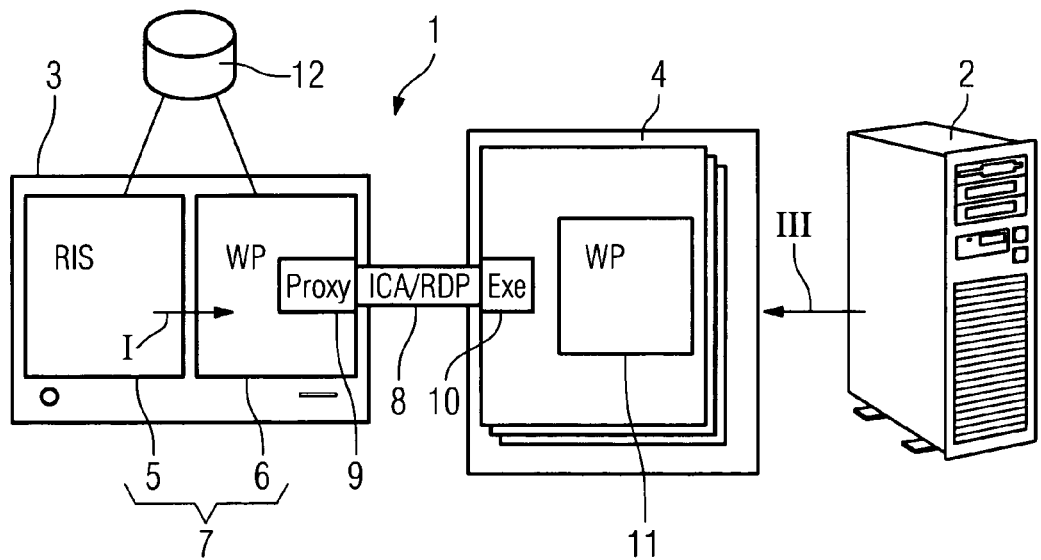

METHOD FOR PROVIDING IMAGE OBJECTS IN A MEDICAL IMAGE INFORMATION SYSTEM, AND MEDICAL IMAGE INFORMATION SYSTEM

PRIORITY STATEMENT

The present application hereby claims priority under 35 U.S.C. §119 on German patent application number DE 10 2007 044 599.9 filed Sep. 19, 2007, the entire contents of which is hereby incorporated herein by reference.

FIELD

Embodiments of the invention generally lie in the technical field of digital image information systems and generally relate to a method for providing image objects in a medical image information system and/or to a medical image information system which is suitable for carrying out the method.

BACKGROUND

Medical image information systems are increasingly being used in clinics and relatively large doctor's surgeries to store, display, process and make findings on image objects. PACS systems (PACS=Picture Archiving and Communications System) which were originally used purely for the purpose of image data management are nowadays usually merged with administratively oriented information systems, such as radiology information systems (RIS) or hospital information systems (HIS), to form integrated medical image information systems.

In such integrated medical image information systems, medical images produced using imaging modalities are sent, via; a data network, in the form of pixel data to a data storage device and are stored there together with the administrative text data belonging to the image data, for example patient name, date of birth, patient number, device number, date of examination, study number and so forth. The pixel-based image data of the image objects are usually stored in one or more image data stores and the administrative text data are stored in a separate text data store associated with the image data stores. The image data are typically first of all stored in a short-term image data store, for example a non-volatile RAID store (RAID=Redundant Array of Independent Disks). From there, they may be interrogated within a very short space of time by computer-assisted screen workstations, so-called findings consoles. After a period of time has elapsed or after findings have been made, the pixel data are transmitted to a long-term image data store in order to be permanently archived, which long-term image data store is, for example, in the form of a so-called jukebox with a plurality of tape or disk stores.

The medical image information system is typically in the form of a server/client architecture, the screen workstations (clients) being connected to the data stores (servers), which are used to store data, for data purposes by way of a communication network.

The image objects which are stored in the server are displayed on the basis of a user request made using a graphical user interface GUI which is made available to the screen workstations by an application which runs locally there. In order to display an image object in a graphical user interface, for example in order to view, process or make findings on the images, the image object is transmitted from the image data store containing the image object; usually a short-term image data store, to a local data store of the screen workstation. For this purpose, an item of information, which is contained in the text database and relates to which image data belong to a particular image object and in which image database these image data are stored, is usually first of all acquired and the image object is then loaded into the local data store of the client by sequentially transmitting the data to the client via the communication network.

The integrated medical image information system is usually controlled by means of applications which are locally implemented in the clients and make it possible, in particular, for users to optionally carry out user interactions, such as the request of image objects. An application is generally a computer program containing machine-readable control commands which cause the image information system to carry out a desired method sequence.

For this purpose, at least two applications are implemented in the clients of integrated medical RIS/PACS or HIS/PACS image information systems. These applications are a text data application, which can be associated with the original RIS system (or HIS system) and is used solely to manage administrative text data of the image objects, and an image data application which can be associated with the original PACS system and is used solely to manage pixel-based image data of the image objects. It goes without saying that the two applications may be considered to be a single application having subfunctions associated with the text data application and the image data application.

Image objects are displayed by the client, under the control of the image data application, in the form of two-dimensional slice images or three-dimensional volume displays, the volume displays first of all having to be determined by computer from the slice images ("3D rendering"). Text data are displayed by the text data application. The operations of displaying and processing the pixel-based image data, in particular 3D rendering, require a relatively high computing power of the client, with the result that the hardware of the client must be designed in an appropriately powerful manner in order to execute the image data application, which, however, is associated with relatively high costs on account of the usual multiplicity of clients in the same image information system.

SUMMARY

In at least one embodiment of the present invention, a medical image information system and/or a method are disclosed for providing image objects in such an image information system, which enables a less powerful design of the clients.

According to at least one embodiment of the invention, a medical image information system and/or a method are disclosed for providing image objects in such an image information system.

According to at least one embodiment, the invention shows a medical image information system for managing image objects in a server/client architecture. The image information system comprises a PACS server (that is to say an electronic data processing device) which is provided with at least one non-volatile data store for storing image and text data of image objects, a terminal server which is (networked) connected to the PACS server for data purposes, and at least one terminal client which is (networked) connected to the terminal server for data purposes and is in the form of a screen workstation provided with a display apparatus.

As usual, the terminal server is able to produce screen outputs on the terminal client and is able to receive user inputs, such as keystrokes and mouse inputs, from the terminal client. For this purpose, a transmission protocol is implemented between the terminal server and the terminal client, which protocol governs the transmission of the screen contents, which are to be displayed on the terminal client, from the terminal server to the terminal client and the transmission of the user inputs, which are made on the terminal client, to the terminal server using their data connection.

In order to manage image objects, at least two applications which each provide a graphical user interface on the display apparatus of the client are implemented in the image information system. As explained initially, these applications are a text data application, which is used solely to manage (in particular to acquire and display) the text data belonging to image objects, and an image data application which is used solely to manage (in particular to acquire and display) the pixel-based image data belonging to image objects. It goes without saying that the two graphical user interfaces provided by the text data and image data applications may be considered to be a single graphical user interface which is implemented by means of the two applications.

The important factor in this case is that, in the image information system according to at least one embodiment of the invention, the text data application is implemented solely locally in the terminal client and is executed there and the image data application is implemented solely locally in the terminal server and is executed there. The transmission protocol implemented between the terminal server and the terminal client is designed in this case in such a manner that the text data application can call the image data application and vice versa. In particular, this makes it possible to transfer commands, such as the display of particular image objects and the reading of the corresponding image data from the PACS server, from the text data application to the image data application.

At least one embodiment of the invention also relates to a method for providing image objects in a medical image information system as described above, in which an image object which is stored in the PACS server is transmitted to the terminal server, in particular on the basis of a user request or automatically, under the control of the image data application, pixel-based screen contents for a graphical display of the image object by the display apparatus (in particular graphical user interface) of the terminal client, under the control of the image data application, are determined by the terminal server, and the screen contents for the image object, which are determined by the terminal server, are then displayed by the terminal client. In this case, the image object is advantageously transmitted from the PACS server to the terminal server on the basis of a user request for an image object which is stored in the image storage system, which request is made using the graphical user interface.

Since the particularly computing-intensive display and processing of image data of image objects are carried out on the terminal server in the medical image information system according to at least one embodiment of the invention, it is advantageously possible for the first time to provide the clients with relatively little processor power, with the result that the investment costs for such an image information system can be considerably reduced.

BRIEF DESCRIPTION OF THE DRAWINGS

The invention is now explained in more detail using an example embodiment, reference being made to the accompanying figures.

FIG. 1 shows a diagrammatic illustration of an example embodiment of the medical image information system according to the invention;

FIG. 2 shows a further diagrammatic illustration of the image information system of FIG. 1.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The two figures illustrate a medical image information system, which is denoted overall by the reference number 1 and is an integrated RIS/PACS image information system, and a method for providing image objects in this image information system.

The integrated medical RIS/PACS image information system 1 accordingly includes a PACS server which is denoted overall by the reference number 2 and is used to store and archive image and text data of image objects. In this case, the image objects respectively comprise pixel-based image data and administrative text data, the image data being acquired by imaging modalities, such as computer tomographs and magnetic resonance tomographs, which are networked to the image storage system 2, which is not illustrated in the figures.

In the PACS server 2, the administrative text data are stored in a text data store and the image data are stored in a plurality of image data stores, the text data store being different from the image data stores. Text and image data of the same image object are associated with one another using so-called identifiers, for example.

Furthermore, the integrated medical RIS/PACS image information system 1 includes a computer-assisted screen workstation 3 which is provided with a display apparatus (display) and is connected to the PACS server 2 for data purposes with the interposition of a terminal server 4 which is connected both to the screen workstation 3 and to the PACS server 2 for data purposes. The terminal server 4 is set up to functionally emulate different functions of the screen workstation 3 in a suitable manner. Although the figures illustrate only an individual screen workstation 3, a plurality of screen workstations may equally be provided in the image information system 1 according to an embodiment of the invention.

Two different applications are implemented in the integrated medical RIS/PACS image information system 1 in order to manage image objects. These applications are an image data application "WP" 11 (WP=Work Place), which is used solely to manage, that is to say in particular to acquire, store, read, process, archive and display, pixel-based image data of image objects, and a text data application "RIS" (RIS=Radiology Information System) which is used solely to manage, that is to say in particular to acquire, store, read, process, archive and display, text data of image objects. In the medical image information system 1, the text data application is implemented in the screen workstation 3 and is executed locally there, whereas the image data application 11 is implemented in the terminal server 4 and is executed locally there.

The applications implemented and executed in the image information system 1 provide a graphical user interface 7 in the display apparatus of the screen workstation 3, which user interface is composed of two graphical user subinterfaces, namely a first graphical user subinterface RIS 5, which is provided by the text data application, and a second graphical user subinterface WP 6 which is provided by the image data application. The image data application WP is thus executed in the terminal server 4 and only the second graphical user interface WP 6 is displayed on the display apparatus of the screen workstation 3.

A transmission protocol which is set up in the image information system 1 for transmitting data between the terminal server 4 and the terminal client 3 and may be a conventional transmission protocol for controlling the transmission of data between the terminal server and the terminal client is used to transmit user inputs, such as keystrokes and mouse pointer movements, which are made on the screen workstation or terminal client 3, to the terminal server 4. Furthermore, the transmission protocol makes it possible to send the screen output to the terminal client 3 and to display it on the display apparatus of the latter. In this case, the transmission protocol may be based, for example, on commercially available protocols such as "RDP" (RDP=Remote Desktop Protocol) from Microsoft and ICA (ICA=Independent Computer Architecture) and "Metaframe" from Citrix.

If a user request for image objects for a particular patient XY is made on the screen workstation 3 in the medical image information system 1, for example by a user inputting the name of the patient XY or another patient identifier using the user interface RIS 5, the text data application RIS running on the terminal client 3 calls the image data application WP 11 running on the terminal server 4 using the command "load image data for the patient XY from the PACS server 2" (steps I, II). The terminal server 4 then reads the corresponding image data from the PACS server 2 (step III). After the image data have been processed in an appropriate manner, for example after volume displays have been calculated by the image data application WP 11, the screen contents to be displayed are transmitted from the terminal server 4 to the terminal client 3 and the pixel-based image data of the requested image objects are displayed in the graphical user interface WP 6 of the display apparatus of the terminal client 3. In addition, the administrative text data belonging to the requested image objects are read from the PACS server 2 by the text data application locally executed in the screen workstation 3 and are displayed in the graphical user interface RIS 5 of the display apparatus of the terminal client 3.

As can be gathered in more detail from FIG. 2, a data transmission channel 8, which is governed in this case by the ICA/RDP protocols, for example, is set up for the purpose of transmitting data between the screen workstation 3, which is used as the terminal client, and the terminal server 4. In order to make it possible for the text data application to call the image data application and for commands to load image data from the PACS server 2 to be transmitted from the screen workstation 3 to the terminal server 4, the transmission protocol for transmitting data between the screen workstation 3 and the terminal server 4 is modified in such a manner that a proxy driver 9 is implemented in the screen workstation 3, which proxy driver transmits commands issued by means of user inputs, in particular for loading image data from the PACS server 2, to the terminal server 4 via the data transmission channel 8. Furthermore, the transmission protocol is modified to the effect that an executable program file "Exe"

(Exe=executable) is implemented in the terminal server 4, which program file reads the data transmission channel 8 for commands, for example for loading image data from the PACS server 2, and interprets the corresponding commands. The proxy driver 9 itself reads the commands to be transmitted to the terminal server 4 from a memory mapped file MMF 12 which, as usual, is used to transmit commands and arguments in a process-spanning manner.

Since the image data application WP 11 is executed in the terminal server 4 in the image information system 1, computing-intensive processing of pixel-based image data of image objects is carried out solely in the terminal server 4. The screen workstation 3 can therefore be provided with correspondingly little computing power in a cost-effective manner and can be designed, in particular, as a so-called "thin client" or terminal which is essentially restricted to the input and output of data.

Further features of the invention emerge from the following description:

PACS systems enable a completely digital image workflow in a hospital. The system is not only intended for use in an individual hospital but rather may encompass a plurality of hospitals and medical centers. A central terminal server (presentation server) which ensures the connection between the screen workstation and the PACS system (OPM+SDM) is provided. The terminal server provides a user with individual applications which behave like locally installed programs. In reality, however, only the screen contents are transmitted from the terminal server to the client, whereas the applications run entirely on the server.

An embodiment of the invention makes it possible to connect a further application, which is locally installed on the workstation, to the terminal server. The connection is implemented, for example, using RDP or IRA in order to make it possible for client applications which are running locally on the client to access the remotely running server application and vice versa (server applications may call client applications). In the exemplary embodiment shown, the client application is a radiology information system (RIS). A connection to the server application is implemented by modifying the remote desktop protocol provided by the terminal server. The RIS application can call the server application WP, which runs on the terminal server, in order to load images for a particular patient. It is not necessary for the user to change the application. The interface of the client computer for enabling communication across processes is implemented using a memory mapped file (MMF). The RIS application calls a modified but standardized interface which puts the command into the MMF. A proxy driver which uses ICA/RDP to transmit the call to the terminal server, where an executable program detects the call and directly calls the WP application, runs on the client.

Advantages of at least one embodiment of the invention result from a cost saving, from a reduction in the management complexity since the software need not be installed on all clients but only on the terminal server, from the possibility of providing relatively low-power clients, from flexible access options and efficient management in heterogeneous environments. Furthermore, mobile workstations, in particular handheld computers, can be used to display the images.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing image objects in a medical image information system including a PACS server having at least one non-volatile data store for storing the image objects, a terminal server connected to the PACS server for data purposes, and at least one terminal client connected to the terminal server for data purposes, a text data application, used solely to manage text data of image objects, being implemented in the terminal client, and an image data application, used solely to manage pixel-based image data of image objects, being implemented in the terminal server, the method comprising:

transmitting an image object from the first server to the other terminal server, under the control of the image data application;

determining, by the other server, pixel-based screen contents for a graphical display of the image object by the terminal client, under the control of the image data application; and displaying, by the terminal client, the screen contents for the image object determined by the other server.

2. The method as claimed in claim 1, wherein the image object is transmitted from the first server to the other server on the basis of a user input made using a graphical user interface.

3. The method as claimed in claim 2, wherein the first server is a PACS server and wherein the other server is a terminal server.

4. The method as claimed in claim 1, wherein the transmitting of an image object to the other server is done on the basis of a user request, under the control of the image data application.

5. The method as claimed in claim 4, wherein the image object is transmitted from the first server to the other server on the basis of a user input made using a graphical user interface.

6. The method as claimed in claim 5, wherein the first server is a PACS server and wherein the other server is a terminal server.

7. The method as claimed in claim 4, wherein the first server is a PACS server and wherein the other server is a terminal server.

8. The method as claimed in claim 1, wherein the first server is a PACS server and wherein the other server is a terminal server.

9. A medical image information system for managing image objects, comprising:
- a PACS server including at least one non-volatile data storage device to store image objects;
- a terminal server, connected to the PACS server for data purposes; and
- at least one terminal client, connected to the terminal server for data purposes, a text data application, used solely to manage text data of image objects, being implemented solely locally in the at least one terminal client, and an image data application, used solely to manage pixel-based image data of image objects, being implemented in the terminal server.

10. A non-transitory computer readable medium including program segments for, when executed on a computer device, causing the computer device to implement the method of claim 1.

* * * * *